United States Patent [19]
Del Corral et al.

[11] Patent Number: 5,709,880
[45] Date of Patent: Jan. 20, 1998

[54] METHOD OF MAKING TABLETIZED IONENE POLYMERS

[75] Inventors: L. Fernando Del Corral, Memphis; Percy A. Jaquess, Tigrett; Wallace E. Puckett; Russel E. Fues, both of Memphis, all of Tenn.

[73] Assignee: Buckman Laboratories International, Inc., Memphis, Tenn.

[21] Appl. No.: 500,466

[22] Filed: Jul. 10, 1995

[51] Int. Cl.$^6$ .......................... A61N 25/08; A61K 31/785
[52] U.S. Cl. .......................... 424/464; 424/408; 424/468; 424/78.1; 424/78.12; 210/735; 528/488; 528/499; 523/414; 523/420; 524/394; 524/400; 524/456; 524/922
[58] Field of Search .......................... 424/408, 78.1, 424/78.12, 464, 468; 210/735; 528/488, 499; 523/414, 420; 524/394, 400, 922, 456

[56] References Cited

U.S. PATENT DOCUMENTS

| | | | |
|---|---|---|---|
| Re. 28,808 | 5/1976 | Panzer et al. | 260/2 BP |
| 3,738,945 | 6/1973 | Panzer et al. | 260/2 BP |
| 3,778,476 | 12/1973 | Rembaum et al. | 260/567.6 P |
| 3,874,870 | 4/1975 | Green et al. | 71/67 |
| 3,894,946 | 7/1975 | Panzer et al. | 210/54 |
| 3,894,947 | 7/1975 | Panzer et al. | 210/54 |
| 3,930,877 | 1/1976 | Aitken | 106/287 |
| 3,931,319 | 1/1976 | Green et al. | 260/567.6 |
| 4,025,627 | 5/1977 | Green et al. | 424/248.4 |
| 4,027,020 | 5/1977 | Green et al. | 424/248.56 |
| 4,080,358 | 3/1978 | Krumel et al. | 524/922 |
| 4,089,977 | 5/1978 | Green et al. | 424/329 |
| 4,104,161 | 8/1978 | Wein | 210/54 |
| 4,111,679 | 9/1978 | Shair et al. | 71/67 |
| 4,147,627 | 4/1979 | Goodman | 210/58 |
| 4,164,521 | 8/1979 | Goodman | 525/187 |
| 4,166,041 | 8/1979 | Goodman | 252/180 |
| 4,269,723 | 5/1981 | Barford et al. | 252/106 |
| 4,310,434 | 1/1982 | Choy et al. | 252/174.21 |
| 4,396,552 | 8/1983 | Knobloch et al. | 260/429.7 |
| 4,477,363 | 10/1984 | Wong et al. | 252/134 |
| 4,506,081 | 3/1985 | Fenyes et al. | 548/523 |
| 4,581,058 | 4/1986 | Fenyes et al. | 71/67 |
| 4,606,773 | 8/1986 | Novak | 106/213 |
| 4,631,305 | 12/1986 | Guyer et al. | 523/400 |
| 4,654,341 | 3/1987 | Nelson et al. | 514/241 |
| 4,683,072 | 7/1987 | Holdt et al. | 252/102 |
| 4,698,264 | 10/1987 | Steinke et al. | 424/408 |
| 4,769,155 | 9/1988 | Dwyer | 210/728 |
| 4,778,813 | 10/1988 | Fenyes et al. | 514/357 |
| 4,820,449 | 4/1989 | Menke et al. | 252/544 |
| 4,876,003 | 10/1989 | Casberg | 210/169 |
| 4,911,858 | 3/1990 | Bunczk et al. | 252/106 |
| 4,961,872 | 10/1990 | Sinclair | 252/186.37 |
| 4,970,211 | 11/1990 | Fenyes et al. | 514/252 |
| 5,051,124 | 9/1991 | Pera | 71/67 |
| 5,093,078 | 3/1992 | Hollis et al. | 422/16 |
| 5,128,100 | 7/1992 | Hollis et al. | 422/14 |
| 5,142,002 | 8/1992 | Metzner | 525/540 |
| 5,205,955 | 4/1993 | Bunczk et al. | 252/102 |
| 5,419,897 | 5/1995 | Drake et al. | 424/78.1 |

FOREIGN PATENT DOCUMENTS

| | | | |
|---|---|---|---|
| 0 371 308 | 6/1990 | European Pat. Off. | |
| 0526437 | 2/1993 | European Pat. Off. | |
| 2806707 | 8/1978 | Germany | 424/78.1 |
| 0791281 | 2/1958 | United Kingdom | 424/78.1 |
| 1 601 123 | 10/1981 | United Kingdom | |
| WO 91/18510 | 12/1991 | WIPO | |
| WO 92/13528 | 8/1992 | WIPO | |

OTHER PUBLICATIONS

Derwent Publications Ltd., London, GB; AN 83-40328K and JP 58/46003 (abstract; 6/1983.
A. Rembaum, Biological Activity of Ionene Polymers, Applica Polymer Symposium #22 pp. 299-317 (1973).
O. May, "Polymeric Anti-Microbial Agents", Disenfection, Sterilization, and Preservation, S. Block, Ed., pp. 322-333, (Lea and Febiger, Phil., 1991).
FMC Tablet Processing, 8 pages, 1988.
J.T. O'Conner and S.K. Kapoor, "Small Quantity Field Disinfection", Jour. AWWA, p. 80, 1970.

*Primary Examiner*—Andrew E.C. Merriam
*Attorney, Agent, or Firm*—Morgan, Lewis & Bockius LLP

[57] ABSTRACT

Tabletized ionene polymers, methods for their preparation and their use in water treatment is described. The tablet contains about 5 to about 60 percent by weight of an ionene polymer, about 40 to about 95 percent by weight of a salt carrier matrix, 0 to about 10 percent by weight of a disintegration rate regulator, and 0 to about 10 percent by weight of an anticaking agent. The tablets may be made by mixing an aqueous solution of an ionene polymer with a carrier matrix to form a moist mass, drying the moist mass to form granules, reducing the granule size to form a powder, and compressing the powder into a tablet. The tablets are useful in a wide variety of water treatment applications. Accordingly, the specification describes a method for controlling the growth of microorganisms in an aqueous system. Using the method, one treats an aqueous system with an ionene polymer in an amount effective to control the growth of at least one microorganism. The ionene polymer is contained in a tablet of the invention.

13 Claims, 2 Drawing Sheets

METHOD OF MAKING TABLETIZED IONENE POLYMERS

BACKGROUND OF THE INVENTION

1. Field of the Invention

The present invention relates to tabletized ionene polymers, methods for their preparation, and their use in water treatment.

2. Description of Related Art

Biological fouling is a persistent nuisance or problem in all varieties of aqueous systems. Biological fouling can have a direct adverse economic impact when it occurs in industrial process waters, for example in cooling waters, metal working fluids, or other recirculating water systems such as those used in papermaking or textile manufacture. If not controlled, biological fouling of industrial process waters can interfere with process operations, lowering process efficiency, wasting energy, plugging the water-handling system, and even degrading product quality.

Biological fouling of recreational water systems such as pools, spas, or decorative (or ornamental) water systems, (e.g., ponds or fountains), can severely detract from people's enjoyment of them. Biological fouling often results in objectional odors. More importantly, particularly in recreational waters, biological fouling can degrade the water quality to such an extent that it becomes unfit for use and may even pose a health risk.

Sanitation waters, like industrial process waters and recreational waters, are also vulnerable to biological fouling and its associated problems. Sanitation waters include, for example, toilet water, cistern water, and sewage treatment waters. Due to the nature of the waste contained in sanitation waters, these water systems are particularly susceptible to biological fouling.

Ionene polymers have often been used to control or prevent biological fouling, including biofilm and slime formation, in aqueous systems. Advantageously, ionene polymers, or polymeric quaternary ammonium compounds (polyquats), generally do not foam excessively in water or aqueous systems, do not irritate skin, and exhibit extremely low toxicity to warm-blooded animals. These characteristics along with their ability to control or prevent biological fouling cause ionene polymers to be excellent choices for water treatment.

Ionene polymers are commonly sold and used as liquid compositions such as aqueous solutions or formulations. Solid forms, including tablets, of ionene polymers have been disclosed in U.S. Pat. Nos. 5,142,002 and 5,419,897. Other water treatment chemicals are often sold in solid forms, such as tablets or pucks. The following patents describe various solid forms of water treatment chemicals for use in a number of different aqueous systems: U.S. Pat. Nos. 4,310,434, 4,396,522, 4,477,363, 4,654,341, 4,683,072, 4,820,449, 4,876,003, 4,911,858, 4,961,872, and 5,205,955 as well as U.K. Patent No. 1,601,123, PCT Application WO 91/18510, PCT Application WO 92/13528, and European patent Application No. 0 526 437 A1.

In some applications solid forms provide advantages over liquid compositions. Well formulated solid forms provide increased stability and reduce exposure to chemicals, solvents, or vapors. In a solid, different ingredients may be successfully combined where such a combination in a liquid might lead to unwanted reactions and potential loss of activity. Using a solid form, a chemical composition can often be packaged and shipped in a more concentrated form than with liquid compositions. Solid forms can also reduce or eliminate concerns regarding the liquid spilling or containers breaking during shipping or handling.

At the point of use, solid forms may also offer additional advantages over liquid formulations. Solid forms provide unit dosing and a uniform delivery system reducing errors in amounts used. Solid forms of water treatment chemicals can also be formulated to provide sustained or prolonged release of chemical to the aqueous system.

As shown by the above discussion, it would be desirable to combine the biological efficacy of an ionene polymer with the advantages of a solid formulation. Solid forms of ionene polymers would compliment the utility of liquid ionene polymer formulations. Accordingly, there exists a need for solid form of an ionene polymer useable in water treatment and other uses.

SUMMARY OF THE INVENTION

The present invention relates to tabletized ionene polymers. A tablet according to the invention comprises from about 40 to about 95 percent by weight of a salt carrier matrix, from about 5 to about 60 percent by weight of an ionene polymer, preferably adsorbed on the salt carrier matrix, from about 0 to about 20 percent by weight of a disintegration rate regulator, and from 0 to about 20 percent by weight of an anticaking agent. A tablet of the invention has a hygroscopicity index of no more than about 3 percent by weight. In other words, on standing for 30 days in air at approximately 25° C. and approximately 70 percent humidity, a tablet of the invention adsorbs only about 3 percent by weight of moisture. Thus, the tablets of the invention have very low moisture uptake.

The tablets may be made by mixing an aqueous solution of an ionene polymer with a salt carrier matrix to form a moist mass. The moist mass is dried to form granules and the size of the granules reduced to form a powder. The powder is then compressed into a tablet.

The tablets of the invention may be used in a wide variety of water treatment applications. Accordingly, the present invention provides a method for controlling the growth of microorganisms in an aqueous system. A tablet of the invention may be used to treat an aqueous system with an effective amount of an ionene polymer to control the growth of at least one microorganism.

DETAILED DESCRIPTION OF THE INVENTION

Figure 1:
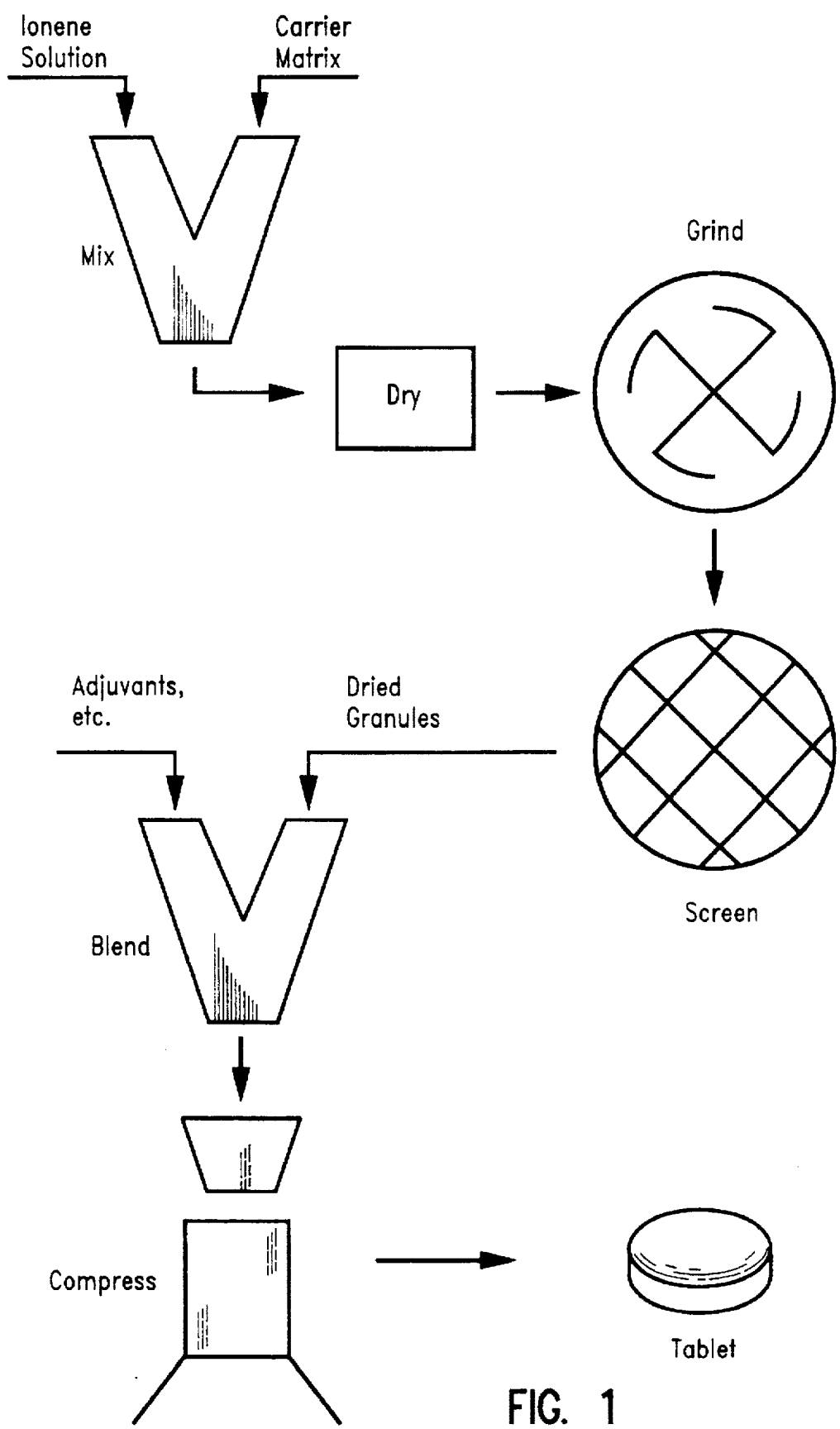
FIG. 1 depicts a general method for making a tabletized ionene polymer.

A first embodiment of the invention relates to a tablet comprising a salt carrier matrix and an ionene polymer preferably adsorbed onto that matrix. "Tablet" forms include tablets themselves as well as other solid forms or shapes known in the art such as sticks, pucks, briquets, pellets, and the like. In other words, any shape tablet may used in accordance with the present invention and is only limited by the ingenuity of the tool and dye maker.

A typical ionene polymer tablet of the present invention comprises from about 40 to about 95 percent by weight of a salt carrier matrix, from about 5 to about 60 percent by weight of an ionene polymer preferably adsorbed on the salt carrier matrix, from 0 to about 20 percent by weight of a disintegration rate regulator, and from 0 to about 20 percent by weight of an anticaking agent. A tablet of the invention has a hygroscopicity index of no more than about 3 percent by weight.

The hygroscopicity index is a measure of moisture uptake by the tablet. Tablets having high hygroscopicity indexes tend to fall apart or disintegrate, even in air, causing the tablets to be unsuitable for use in water treatment applications. A tablet's hygroscopicity index measures the tablet's moisture uptake upon standing for 30 days in air at approximately 25° C. and approximately 70 percent humidity. In general, these conditions represent ambient room temperature and humidity.

Expressed a percentage change in tablet weight, the hygroscopicity index provides a good measure of a tablet's stability. This is particularly true in tablets of the present invention which combine a salt carrier matrix with an ionene polymer-two hygroscopic components. Advantageously, the tablets combine these hygroscopic components and arrive at a tablet that is stable at ambient conditions. Yet, both components are water soluble and, when used in water treatment applications, both leave little or no residue in the aqueous system.

Tablets of the invention have a hygroscopicity index of no more than 3 percent by weight. Thus, the tablets have very low moisture uptake adsorbing only about 3 percent by weight of moisture. Preferred tablets have a hygroscopicity index of from 1.0 to 3.0 percent by weight and most preferred tablets have a hygroscopicity index of no more than 1.0 percent by weight. As seen in the Examples below, some tablets of the invention have a hygroscopicity index of 0.

The size of a tablet according to the invention may vary depending upon its intended use. For example, water treatment tablets used in toilet bowl water range in size from approximately 50 to 100 grams while those used to treat swimming pools or cooling tower water may be approximately 200 to 400 grams. As one of ordinary skill knows, the tablet size depends to some extent on the size and needs of the particular aqueous system. More than one tablet may be used to treat the system.

A tablet of the invention may contain mixtures of one or more ionene polymers with other active compounds or additives commonly used in water treatment or to prepare tablets. Thus, the tablets may contain a variety of excipients known in the art such as biocidal adjuvants, dyes or other coloring agents, and perfumes or fragrances. Other components known in the art such as fillers, binders, glidants, lubricants, or antiadherents may also be included. These latter components may be included to improve tablet properties and/or the tableting process. Various components and preferred embodiments of the tablets of the invention are discussed below.

Ionene Polymers

Any ionene polymer may be used in the present invention. The tablet of the present invention contains about 5 to 60 percent by weight of an ionene polymer. More preferably, the tablet contains 10 to 50 percent by weight of an ionene polymer and most preferably, 20 to 30 percent by weight. The tablet may contain one ionene polymer or a mixture of ionene polymers. In a preferred embodiment, the ionene polymer is adsorbed on the salt carrier matrix.

Ionene polymers or polymeric quaternary ammonium compounds (polyquats), i.e., cationic polymers containing quaternary nitrogens in the polymer backbone (also known as polymeric quats or polyquats), belong to a well-known class of compounds. The biological activity of this class of polymers is also known. See, e.g., A. Rembaum, *Biological Activity of Ionene Polymers*, Applied Polymer Symposium No. 22, 299–317 (1973) and O. May, "Polymeric Antimicrobial Agents" in *Disinfection, Sterilization, and Preservation*, S. Block, Ed., 322–333 (Lea & Febiger, Philadelphia, 1991). Ionene polymers have a variety of uses in aqueous systems such as microbicides, bactericides, and algicides as well as controlling, even preventing, biofilm and slime formation. U.S. Pat. Nos. 3,874,870, 3,931,319, 4,027,020, 4,089,977, 4,111,679, 4,506,081, 4,581,058, 4,778,813, 4,970,211, 5,051,124, 5,093,078, 5,142,002 and 5,128,100, which are incorporated here by reference, give various examples of these polymers, their preparation, and their uses.

Any ionene polymer or mixture of ionene polymers may be used to practice this invention. Ionene polymers may be classified according to the repeating unit found in the polymer. The repeating unit results from the reactants used to make the ionene polymer.

A first preferred type of ionene polymer comprises the repeating unit of formula I:

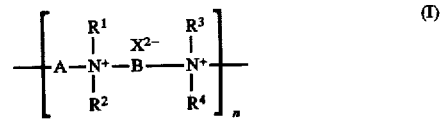

In this formula, $R^1$, $R^2$, $R^3$, and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group. Preferably, $R^1$, $R^2$, $R^3$ and $R^4$ are all methyl or ethyl.

The group "A" is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, symmetric or asymmetric di-$C_1$–$C_{10}$-alkyleneether, arylene, arylene-$C_1$–$C_{10}$-alkylene, or $C_1$–$C_{10}$-alkylenearyl-$C_1$–$C_{10}$ alkylene. Preferably, "A" is a divalent $C_1$–$C_5$ alkylene, $C_2$–$C_5$ alkenylene, $C_2$–$C_5$ hydroxyalkylene, or symmetric di-$C_2$–$C_5$-alkyleneether, and most preferably "A" is —$CH_2CH_2CH_2$—, —$CH_2CH(OH)CH_2$— or —$CH_2CH_2OCH_2CH_2$—.

The group "B" is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, arylene, arylene-$C_1$–$C_{10}$-alkylene, or $C_1$–$C_{10}$-alkylenearyl-$C_1$–$C_{10}$-alkylene. Preferably, "B" is $C_1$–$C_5$ alkylene, $C_2$–$C_5$ alkenylene, $C_2$–$C_5$ hydroxyalkylene, arylene, arylene-$C_1$–$C_5$-alkylene, or $C_1$–$C_5$ alkylenearyl-$C_1$–$C_5$-alkylene. Most preferably "B" is —$CH_2CH_2$—, —$CH_2CH_2CH_2$—, —$CH_2CH_2CH_2CH_2$—, or —$CH_2(CH_2)_4CH_2$—.

The counter ion, $X^{2-}$, is a divalent counter ion, two monovalent counter ions, or a fraction of a polyvalent counter ion sufficient to balance the cationic charge in the repeating unit which forms the ionene polymer backbone. Preferably, $X^{2-}$ is two monovalent anions selected from a halide anion and a trihalide anion and more preferably, chloride or bromide. Ionene polymers having trihalide counter ions are described in U.S. Pat. No. 3,778,476, the disclosure of which is incorporated here by reference.

The ionene polymers having the repeating unit of formula I may be prepared by a number of known methods. One method is to react a diamine of the formula $R^1R^2N$—B—$NR^1R^2$ with a dihalide of the formula X—A—X. Ionene polymers having this repeating unit and methods for their preparation are described, for example, in U.S. Pat. Nos. 3,874,870, 3,931,319, 4,025,627, 4,027,020, 4,506,081 and 5,093,078, the disclosures of which are incorporated here by reference. The biological activity of ionene polymers having the repeating unit of formula I is also described in these patents.

Among the ionene polymers with a repeating unit of formula I, a particularly preferred ionene polymer is poly [oxyethylene-(dimethyliminio)ethylene(dimethyliminio) ethylene dichloride. In this ionene polymer of formula I, $R^1$, $R^2$, $R^3$ and $R^4$ are each methyl, A is —$CH_2CH_2OCH_2CH_2$—, B is —$CH_2CH_2$—, and $X^{2-}$ is 2 $Cl^-$, and the average molecular weight is 1,000–5,000. This ionene polymer is available from Buckman Laboratories, Inc. of Memphis, Tenn. as BUSAN® 77 product or WSCP® product, which are each 60% aqueous dispersions of the polymer. BUSAN® 77 and WSCP® are biocides used primarily in aqueous systems, including metalworking fluids, for microorganism control.

Another particularly preferred ionene polymer having a repeating unit of formula I is the ionene polymer where $R^1$, $R^2$, $R^3$ and $R^4$ are each methyl, A is —$CH_2CH(OH)CH_2$—, B is —$CH_2CH_2$—, and $X^{2-}$ is 2 $Cl^-$. This ionene polymer is a reaction product of N,N,N',N'-tetramethyl-1,2-ethanediamine with (chloromethyl)-oxirane, and has an average molecular weight of 1,000–5,000. The polymer is available from Buckman Laboratories, Inc. as BUSAN® 79 product and WSCP® II product, which are each 60% aqueous solutions of the polymer.

A second type of ionene polymer comprises the repeating unit of formula II:

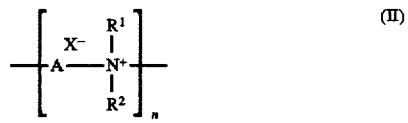

(II)

In formula II, the definitions of $R^1$, $R^2$, and A are the same as those defined above for formula I. $X^-$ is a monovalent counter ion, one half of a divalent counter ion, or a fraction of a polyvalent counter ion sufficient to balance the cationic charge of the repeating unit which forms the ionene polymer. $X^-$ may be, for example, a halide or trihalide anion, and $X^-$ is preferably chloride or bromide.

The ionene polymers having the repeating unit of formula II may be prepared by known methods. One method is to react an amine of the formula $R^1R^2NH$ with a haloepoxide such as epichlorohydrin. Ionene polymers having the repeating unit of formula II are described, for example, in U.S. Pat. Nos. 4,111,679 and 5,051,124, the disclosures of which are incorporated here by reference. The biological activity of ionene polymers having the repeating unit of formula II is also described in these patents.

Preferred ionene polymers having the repeating unit of formula II are those where $R^1$ and $R^2$ are each methyl, A is —$CH_2CH(OH)CH_2$—, and $X^-$ is $Cl^-$. This polymer is obtained as a reaction product of N-dimethylamine with (chloromethyl)oxirane, and has an average molecular weight of 2,000–10,000. The polymer is available from Buckman Laboratories, Inc. as the BUSAN® 1055 product, a 50% aqueous dispersion of the polymer.

Another preferred ionene polymer having the repeating unit of formula II is obtained as a reaction product of dimethylamine with epichlorohydrin, where $R^1$ and $R^2$ are each methyl, A is —$CH_2CH(OH)CH_2$— and $X^-$ is $Cl^-$. This ionene polymer has a 5,000–10,000 average molecular weight, and is available from Buckman Laboratories, Inc. in a 50% aqueous solution as the BUSAN® 1055 product.

A third type of ionene polymer comprises a repeating unit of formula III:

(III)

wherein R is

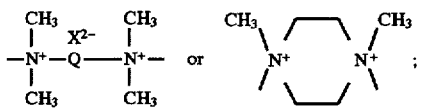

The group Q is —(CHR')p—, —$CH_2$—CH=CH—$CH_2$—, —$CH_2$—$CH_2$—O—$CH_2$—$CH_2$—, —$CH_2$—CH(OH)—$CH_2$—, or —(CHR')$_n$—NH—C(O)—NH(CHR')$_n$—. The group B' is {—$CH_2$—CH(OH)—$CH_2$—$N^+$ $R'_2$—(CHR')$_n$—NH—C(O)—NH)—, $X^-$} or {—(CHR')$_n$—$N^+R'_2$—$CH_2$—CH(OH)—$CH_2$)—, $X^-$}. The variables n and p independently vary from 2 to 12. Each R' is independently hydrogen or a lower alkyl group. $X^{2-}$ is a divalent counter ion, two monovalent counter ions, or a fraction of a polyvalent counter ion sufficient to balance the cationic charge in the group R. $X^-$ is a monovalent counter ion, one half of a divalent counter ion or a fraction of a polyvalent counter ion sufficient to balance the cationic charge in the group B'. Preferably, R' is hydrogen or $C_1$–$C_4$ alkyl, n is 2–6, and p is 2–6. Most preferably, R' is hydrogen or methyl, n is 3 and p is 2. Preferred counter ions for $X^{2-}$ and $X^-$ are the same as those discussed above for formulae I and II.

The polymers of formula III are derived by known methods from bis-(dialkylaminoalkyl) ureas, which are also known as urea diamines. Ionene polymers of the formula III, methods of their preparation, and their biological activities are described in U.S. Pat. No. 4,506,081, the disclosure of which is incorporated here by reference.

Preferred ionene polymers having the repeating unit of formula III are those where R is urea diamine and B' is $CH_2CH(OH)CH_2$, and $X^-$ is $Cl^-$. Available from Buckman Laboratories, Inc., ASTAT product and BL® 1090 product are 50% aqueous dispersions of this ionene polymer. The ionene polymer is obtained as a reaction product of N,N'-bis-[1-(3-(dimethylamino)propyl)]urea and epichlorohydrin, such ionene polymer having an average molecular weight of 2,000–15,000, preferably 3,000–7,000.

Ionene polymers comprising the repeating units of formulae I, II, and III may also be cross-linked with primary, secondary or other polyfunctional amines using means known in the art. Ionene polymers can be cross-linked either through the quaternary nitrogen atom or through another functional group attached to the polymer backbone or to a side chain.

Cross-linked ionene polymers, prepared using cross-linking co-reactants, are disclosed in U.S. Pat. No. 3,738,945 and Reissue U.S. Pat. No. 28,808, the disclosures of which are incorporated here by reference. The Reissue Patent describes the cross-linking of ionene polymers prepared by the reaction of dimethylamine and epichlorohydrin. The cross-linking co-reactants listed are ammonia, primary amines, alkylenediamines, polyglycolamines, piperazines, heteroaromatic diamines and aromatic diamines.

U.S. Pat. No. 5,051,124, the disclosure of which is incorporated here by reference, describes cross-linked ionene polymers resulting from the reaction of dimethylamine, a polyfunctional amine, and epichlorohydrin. U.S. Pat. No. 5,051,124 also describes methods of inhibiting the growth of microorganisms using such cross-linked ionene polymers. Other examples of various cross-linked ionene polymers and their properties are provided in U.S. Pat. Nos. 3,894,946, 3,894,947, 3,930,877, 4,104,161, 4,164,521, 4,147,627, 4,166,041, 4,606,773, and 4,769,155. The disclosures of each of these patents is incorporated here by reference.

A preferred cross-linked ionene polymer has a repeating unit of formula II. This ionene polymer is obtained as a reaction product of dimethylamine with epichlorohydrin, cross-linked with ethylenediamine, where $R^1$ and $R^2$ are each methyl, A is —$CH_2CH(OH)CH_2$— and $X^-$ is $Cl^-$. The ionene polymer has a 100,000–500,000 average molecular weight, and is available from Buckman Laboratories, Inc. in a 50% aqueous dispersion as BUSAN® 1157 product.

Another preferred cross-linked ionene polymer has a repeating unit of formula II, where $R^1$ and $R^2$ are each methyl, A is —$CH_2CH(OH)CH_2$—, $X^-$ is $Cl^-$. The ionene polymer is cross-linked with ammonia. This ionene polymer has a molecular weight of approximately 100,000–500,000, and is available from Buckman Laboratories, Inc. in a 50% aqueous dispersion sold as the BL® 1155 product.

Buckman Laboratories, Inc. products BUSAN® 1099 or BUBOND® 65 are 25% aqueous dispersions of a cross-linked ionene polymer having repeating units of formula II, where $R^1$ and $R^2$ are each methyl, A is —$CH_2CH(OH)CH_2$—, $X^-$ is $Cl^-$, and the cross-linking agent is monomethylamine. This preferred ionene polymer has a molecular weight of approximately 10,000–100,000.

The ionene polymers comprising the repeating units of formulae I, II, or III may also be capped, i.e., have a specific end group. Capping may be achieved by means known in the art. For example, an excess of either reactant used to make the ionene polymer can be employed to provide a capping group. Alternatively, a calculated quantity of a monofunctional tertiary amine or monofunctional substituted or unsubstituted alkyl halide can be reacted with an ionene polymer to obtain a capped ionene polymer. Ionene polymers can be capped at one or both ends. Capped ionene polymers and their microbicidal properties are described in U.S. Pat. Nos. 3,931,319 and 5,093,078, the disclosures of which are incorporated here by reference.

The Salt Carrier Matrix

The salt carrier matrix may be any salt material compatible with the ionene polymer and which can be formed into a tablet. The salt carrier matrix should not interfere with the ionene polymer's biological activity. When other materials are present within the tablet, the salt carrier matrix should not degrade those materials or interfere with their properties or biological activity. In other words, the salt carrier matrix should be inert with respect to the other components of the tablet.

A tablet according to the invention contains from about 40 to about 95 percent by weight of the salt carrier matrix material. More preferably, the tablet contains about 50 to about 80 percent by weight of the matrix material, and most preferably from about 70 to about 80 percent.

Generally, the salt carrier matrix material should be in the form of wettable powder or granules. The particle size of the powder or granules may vary depending upon the size of tablet to be made. Larger tablets are more tolerant of larger particles sizes. Preferably, the carrier matrix has a particle size of 12 mesh or smaller.

The matrix material may be a single salt material or a mixture of two or more salts alone or in combination with other matrix materials. When the carrier matrix contains a mixture of salts, those salts are preferably present in equal amounts, e.g., a mixture of two salts in a 1:1 ratio. As discussed below, the ratio of salts may be adjusted to improve tablet stability, for example, by reducing the hygroscopicity of the carrier matrix.

The salt carrier matrix is preferably a substantially water-soluble matrix. Preferably, the salt carrier matrix is a water-soluble inorganic or organic salt or mixtures of such salts. For purposes of the present invention, water-soluble means having a solubility in water of about 0.2 grams per hundred grams of water at 20° C.

Examples of suitable salts for the carrier matrix include various alkali metal and/or alkaline earth metal sulfates, chlorides, borates, bromides, citrates, acetates, lactates, etc. Specific examples of suitable salts include, but are not limited to, sodium acetate, sodium bicarbonate, sodium borate, sodium bromide, sodium carbonate, sodium chloride, sodium citrate, sodium fluoride, sodium gluconate, sodium sulfate, calcium chloride, calcium lactate, calcium sulfate, potassium sulfate, tripotassium phosphate, potassium chloride, potassium bromide, potassium fluoride, magnesium chloride, magnesium sulfate and lithium chloride. The preferred salts are the inorganic salts, especially the Group 1 or 2 metal sulfates and chlorides. Particularly preferred salts, because of their low cost, are sodium sulfate, and sodium chloride. Sodium chloride may be substantially pure or in the form of rock salt, sea salt, or dendrite salt.

As mentioned above, the salt carrier matrix may contain other carrier materials, preferably in amounts from 0 to about 10 percent by weight of the tablet. These materials are preferably solid and include other carrier materials known in the art. These materials may be solid organic acids such as benzoic, gluconic, or sorbic acid. Use of such materials may allow the salt carrier matrix to have beneficial activity, including biological activity, in the aqueous system. For example, gluconic acid, or its salts, may be used in a carrier matrix. But when the tablet is added to an aqueous system, the gluconic acid may additionally function as a metal chelant to sequester iron and prevent iron oxide staining.

Disintegration Rate Regulators

The tablets of the invention may be formulated for quick disintegration when added to an aqueous system or for sustained release in the aqueous system. Quick disintegration allows for direct dosing of an aqueous system and may be preferable in aqueous systems experiencing problematic microbiological fouling. Sustained release provides a continuous dosing of the system over time. Sustained release tablets may be used for extended prevention or control of biological fouling in an aqueous system such as a swimming pool or a toilet tank. Given the biocidal efficacy of ionene polymers both quick disintegration and sustained release tablets can control biofilm or the growth of microorganisms in an aqueous system. The choice between them, as one of ordinary skill appreciates, depends on the particular use.

To control the rate at which a tablet of the invention dissolves in an aqueous system, a disintegration rate regulator (sometimes called a solubility control agent) may be incorporated into the tablet. Disintegration rate regulators are generally hydrophobic materials which retard dissolution of the tablet. In general, any compound which will coat, trap, or otherwise limit the release of the ionene polymer or tablet disintegration in the aqueous system to achieve sustained or prolonged release may be used. Some disintegration rate regulators may also beneficially serve as a lubricant or mold release agent during the tableting process.

A disintegration rate regulator, or mixtures thereof, may be present in the tablet in an amount from 0 to about 20 percent by weight of the tablet. More preferably, the disintegration rate regulator is present from about 0.25 to about 10 percent by weight and even more preferably from about 0.5 to about 5 percent. Varying the amount of the disintegration rate regulator affects the rate at which the tablet dissolves in an aqueous system. In general, little or no disintegration rate regulator may be used in quick disintegration tablets while larger amounts may be used in sustained release tablets.

The disintegration rate regulator may be a fatty acid or a derivative of a fatty acid. Fatty acids are composed of a chain of alkyl groups containing from about 4 to about 22 carbon atoms (usually even numbered) and have a terminal carboxylic acid group. Fatty acids may be straight or branched, saturated or unstaturated and even aromatic. Fatty acids generally exist as solids, semisolids, or liquids. In the present invention, the fatty acid or its derivative may act not only as a disintegration rate regulator but also as a lubricant or mold release agent while forming the tablet. Fatty acids and their various derivatives are well-known chemicals and are available from a number of suppliers.

Fatty acids which may be used in the present invention include, but are not limited to, butyric acid, decanoic acid, undecylenic acid, palmitic acid, stearic acid, palmitoleic acid, oleic acid, linoleic acid, linolenic acid, and phenyl stearic acid. The fatty acid derivatives which may be used in the present invention include, for example, fatty acid salts, fatty acid amides, fatty acid alkanolamides, fatty alcohols, fatty amines. Mixtures of fatty acids and/or fatty acid derivatives may also be used. For example, tallow fatty acids, palm oil fatty acids, and coconut oil fatty acids are mixtures of fatty acids useable in the present invention. Derivatives of these fatty acid mixtures may also be used; for example, amide derivatives such as dimethyl amide derivatives of tall oil (DMATO) or palm oil (DMAPO).

One group of preferred disintegration rate regulators are those related to stearic acid. These include but are not limited to stearic acid, potassium stearate, magnesium stearate, polyoxyethylene stearate/distearates, polyoxyethylene-2 stearyl ether, glyceryl monostearate, hexaglyceryl distearate, glyceryl palmitostearate, and sodium stearyl fumarate. Magnesium stearate is particularly preferred and is available from Witco Corporation and Mallinkrodt Specialty Chemical Co. The polyoxyethylene stearates/distearates are a series of polyethoxylated derivatives of stearic acid available from ICI Americas, Inc., Wilmington, Del. These include, for example, polyoxyl 6 stearate, polyoxyl 8 stearate, polyoxyl 12 stearate, polyoxyl 20 stearate, polyoxyl 40 stearate, and polyoxyl 50 stearate. Glyceryl monostearate is available from Ashland Chemical Co., Columbus, Ohio. Glyceryl palmitostearate is available from Abatar Corporation, Hickory Hills, N.J. A stearic acid based product having a mixture of compounds is STEROWET product, a mixture of calcium stearate and sodium lauryl sulphate.

Polyoxyethylene sorbitan esters or polysorbate esters, represent another group of preferred disintegration rate regulators. These polysorbate esters are sold as "TWEEN" products available from ICI Americas, Inc., Wilmington, Del. Exemplary esters include polysorbate 81 (TWEEN 81 Product), polysorbate 85 (TWEEN 85 Product), polysorbate 61 (TWEEN 61 Product), polysorbate 65 (TWEEN 65 Product), and polysorbate 21 (TWEEN 21 Product).

Polyoxyethylene ethers, preferably those having alkyl chains of about ten carbons or more, may also be used as disintegration rate regulators in tablets of the invention. These longer alkyl chains increase the hydrophobicity of the ether. Polyoxyethylene ethers are available from ICI Americas, Inc., Wilmington, Del. Examples of these ethers include 2 cetyl ether, 2 stearyl ether, 3 decyl ether, 3 lauryl ether, 3 myristyl ether, 3 cetyl ether, 3 stearyl ether, 4 lauryl ether, 4 myristyl ether, 4 cetyl ether, 4 stearyl ether, 5 decyl ether, 5 lauryl ether, 5 myristyl ether, 5 cetyl ether, 5 stearyl ether, 6 decyl ether, 6 stearyl ether, 7 lauryl ether, 7 myristyl ether, 7 cetyl ether, 7 stearyl ether, 8 lauryl ether, 8 myristyl ether, 8 cetyl ether, 8 stearyl ether, 9 lauryl ether, 10 lauryl ether, 10 tridecyl ether, 10 cetyl ether, 10 stearyl ether, 10 oleyl ether, 20 cetyl ether, 20 isohexadecyl ether, 20 stearyl ether, 20 oleyl ether, and 21 stearyl ether.

Other disintegration rate regulators which may be used include hydrogenated vegetable oils such as the STEROTEX product and Durotex product from Capital City Products of Columbus Ohio. The disintegration rate regulator may also be a wax such as carnauba wax, petroleum ceresin (available from International Wax Refining Co., beeswax (yellow wax) or shellac, (the latter two, available from Van Waters and Rogers). Aliphatic amides such as cocoa amide and octadecanoic amide or hydrogenated tallow amides such as oliamide may also be employed as disintegration rate regulators. Polyethylene amides may also be included in a tablet as a disintegration rate regulator.

A particular disintegration rate regulator may be chosen for use in a tablet on the basis of its properties, for example, ease of use in the tableting process and benefits to the final tablet. The disintegration rate regulator of choice may be slightly, moderately, or very hydrophobic depending upon the particular use. Less hydrophobic regulators are generally used for quick disintegration tablets and more hydrophobic ones for sustained release tablets. For example, sodium stearyl fumarate is less hydrophobic than either stearic acid or magnesium stearate. Thus, sodium stearyl fumarate may be used to increase the rate of dissolution over tablets containing stearic acid or magnesium stearate. Mixtures of disintegration rate regulators may be used to a achieve a desired degree of hydrophobicity or rate of dissolution.

Anticaking Agents

In addition to the salt carrier matrix, an anticaking agent may be present in a tablet of the invention. The anticaking agent may act as binders, desiccants, or absorbents. These anticaking agents should be slightly hygroscopic to non-hygroscopic in nature and may buffer the uptake of moisture by the tablet. Granular or powder forms are preferred. The anticaking agents may be present in amounts from 0 to about 10 percent by weight of the tablet, more preferably, from about 0.1 to about 5 percent by weight, and most preferably from about 0.5 to about 1.5 percent.

Any anticaking agent known in the tableting art may be used in the present invention. Preferably, the anticaking agent is only slightly soluble in water, or more preferably insoluble. Suitable anticaking agents are described in Handbook of Pharmaceutical Excipients, 2d Ed., A. Wade and P. Waller, Eds., (Amer. Pharm. Assoc., 1994). Mixtures of anticaking agents may also be used. Examples of suitable anticaking agents include, but are not limited to, magnesium trisilicate, magnesium oxide, magnesium carbonate, magnesium silicate (e.g., magnesium metasilicate, magnesium orthosilicate), calcium carbonate, calcium silicate (e.g., $CaSiO_3$, $CaSiO_4$, $CaSiO_5$), calcium phosphate (e.g., dibasic calcium phosphate, tribasic calcium phosphate), calcium sulfate, talc, fumed silica, zinc oxide, titanium dioxide, microcrystalline cellulose, 5-chloromethyl-2-oxazolidinone and starch.

Biocidal Adjuvants

The tablets of the invention may contain other biocidal adjuvants commonly used in water treatment. Such adjuvants include, for example, germicides, fungicides, sanitizers, and oxidizing and/or halogen-release agents as well as water clarifiers. These biocidal adjuvants may be present from 0 to about 50 percent by weight of the tablet.

More preferably, they are present from about 5 to about 40 percent by weight of the tablet and most preferably about 10 to about 30 percent. The biocidal adjuvant should preferably be in a solid from. Liquid formulations may used but should not promote undesirable interactions with the ionene polymer or other tablet components.

Suitable germicides include, for example, formaldehyde release agents such as 1,3,5,7-tetra-aza-adamantane hexamethylenetetramine, chlorinated phenols, 1,3,5-tris(ethyl)hexahydro-s-triazine, hexahydro-1,3,5-tris(2-hydroxyethyl)-s-triazine, 1,3-(dihydroxymethyl)-5,5-dimethylhydantoin, N-methylolchloroacetamide, and the like. Hexahydro-1,3,5-tris-(2-hydroxyethyl)-s-triazine is available from Buckman Laboratories, Memphis, Tenn. as BUSAN® 1060 product, a 78.5 percent active solid formulation.

The oxidizing and/or halogen-release agents which can be used in connection with the present invention include, for example, N-chlorinated cyanuric acid derivatives such as sodium dichloroisocyanurate, N-chlorosuccinimide, Chloramine T, dichlorosuccinimide, bromochlorodimethylhydantoin, 1,3-dichloro 5,5-dimethylhydantoin, and alkali metal or alkaline earth metal hypochlorites such as chlorinated sodium tripolyphosphate. Others include sodium perborate, calcium hypochlorite, trichloro-s-trione, and potassium monosulfate. Barium metaborate formulations (modified barium metaborate monohydrate) are available from Buckman Laboratories, Memphis, Tenn. under the trade names BUSAN® 11-M1 product and BUSAN® 11-M2 product.

Other biocidal adjuvants include potassium n-hydroxymethyl-N-methyl thiocarbamate, a 30% active ingredient in BUSAN® 52 product, 30% active ingredient; 2-thiocyanomethylthiobenzothiazole, TCMTB, as BUSAN® 30-C, BUSAN® 30-WB and BUSAN® 1030 products; and MECT 5 product, a mixture of 2.5 by weight and 2.5 percent by weight TCMTB. Each of these products is available from Buckman Laboratories, Memphis, Tenn. The biocide BTC 2125MP40 product may also be used. BTC 2125MP40 product contains 40 percent of a mixture of alkyldimethylbenzylammonium chloride and alkyldimethylethylbenzylammonium chloride and is available from Stepan Chemicals, Northfield, Ill. Chlorhexidine diacetate, another biocidal adjuvant, is the chemical 1,1-hexamethylenebis[5-(4-chloro-2-phenyl)biguanide] diacetate available from Lonza Chemical Co., Fairlawn, N.J.

Conventional water clarifiers may also be included in a tablet of the invention. Clarifiers include, for example, polyDMDAC, aluminum sulfate, and CHITOSAN product.

Dyes and Coloring Agents

A tablet according to the invention may also contain a dye or coloring agent as is known in the art. Dyes or coloring agents may be incorporated in amounts known in the art, for example from 0 to about 5 percent by weight. Examples of suitable dyes for use in non-oxidizing compositions are Alizarine Light Blue B (C.L. 63010), Carta Blue VP (C.L. 24401), Acid Green 2G (C.L. 42085), Astragon Green D (C.L. 42040), Supranol Cyanine 7B (C.L. 42875), Maxilon Blue 3RL (C.L. Basic Blue 80), acid yellow 23, acid violet 17, a direct violet dye (direct violet 51), Drimarine Blue Z-RL (C.L. Reactive Blue 18), Alizarine Light Blue H-RL (C.L. Acid Blue 182), FD&C Blue No.1, FD&C Green No. 3 and Acid Blue No. 9. Additional dyes or coloring agents are described 4,310,434 and 4,477,363, and in the Pharmaceutical Excipients, 2d Ed., A. Wade and P. Waller, Eds., Amer. Handbook of Pharm. Assoc. 1994.

Perfumes

The tablets of the invention may also contain a perfume or fragrance as commonly used in the art. The perfume imparts an acceptable odor to the tablet and the aqueous system, for example toilet water. The perfume or fragrance may be present in known amounts in the art, for example up to 5 percent by weight of the tablet. "Perfumes" include any material having an acceptable odor. Thus, materials giving a disinfectant odor such as essential oils, pine extracts, terpinolenes, ortho phenyl phenol or paradichloro-benzene may be employed. In some embodiments, the essential oils and pine extracts also contribute as plasticizers and function, to a degree, as disintegration rate regulators. Other perfumes or fragrances are disclosed, for example, in U.S. Pat. No. 4,396,522.

Other Adjuvants and Coatings

A tablet of the invention may also include other adjuvants known for use with water treatment tablets. Exemplary adjuvants include, but are not limited to, fillers, binders, glidants, lubricants, or antiadherents, water-softening or chelating agents, stabilizers, etc. Examples of such adjuvants, the properties they add to a tablet, and their uses are described in the patents discussed above relating to solid forms of water treatment chemicals.

Tablets according to the invention may also coated with coatings known in the art. For example, a tablet may be provided with a coating of a water-soluble film, such as polyvinyl alcohol, to make handling more convenient.

Recent advances in coating technology, such as side vented pans, have increased the efficiency of aqueous coating operations. Among the most common ways to apply coatings is through film coating (deposition of a coat through an aqueous or solvent base) or compression coating (compressing a coating around a core tablet). Techniques such as these could also permit the addition of agents to the surface of tablet imparting additional sustained characteristics to the tablets. Somewhat analogous to coatings, the tablet may be manufactured as an inlay tablet or multilayered tablet in which the ionene polymer-containing portion is "sandwiched" between, for example, slow release matrices. This may also create a sustained release tablet according to the invention. For additional reference consult "Pharmaceutical Dosage Forms: Tablets Vols. 1–3", 2d Ed., 1989, H. A. Lieberman, L. Lachman, and J. B. Schwartz, Eds.

A second embodiment of the invention is a method of making a tabletized ionene polymer according to the invention. To make a ionene polymer tablet, an aqueous solution of an ionene polymer is mixed with a salt carrier matrix to form a moist mass. The moist mass is then dried under conditions sufficient to form dry granules. The size of the dry granules is then reduced to yield a powder and the powder compressed into a tablet. The method of the invention and its preferred embodiments are described in more detail below. FIG. 1 depicts a preferred general method.

The first step in making a tabletized ionene polymer according to the invention involves mixing an aqueous solution of at least one ionene polymer with a salt carrier matrix to form a moist mass. The liquid/solid mixing step can be accomplished using conventional blenders/mixers, such as a planetary, ribbon, or double arm mixer.

The amount of ionene polymer solution and carrier matrix used will depend upon the amount of ionene polymer desired in the final tablet. In general, aqueous solutions of ionene polymers are viscous liquids containing from about 25 to 60 percent ionene polymer by weight. Accordingly, since the ionene is in solution, the amount of the amount of the solution used also depends on the concentration of the ionene polymer in the aqueous system.

The mixing step should preferably result in a moist mass with the ionene polymer solution and salt carrier matrix homogeneously mixed. Thus, the amount of ionene polymer solution used should not be so great as to dissolve the carrier or, form a slurry. In general, the ratio of ionene polymer solution to salt carrier matrix should range from about 1:10 to about 2:10. Using an excess amount of solution may not only dissolve the carrier but also cause the mixture to be unsuitable for use in subsequent steps of the method. If this occurs, the excess liquid may be removed from the mixture using techniques known in the art, e.g., by drying as described below. Alternatively, additional carrier matrix may be added until a useable consistency is obtained. Adding carrier matrix will affect the amount of ionene polymer in the final tablet.

Where the carrier matrix contains more than one carrier, those carriers are preferably homogeneously mixed in a separate step before mixing with the ionene polymer solution. Additional tablet components may also be mixed with the carrier matrix prior to mixing with the ionene polymer solution. These other components are preferably added as powders. For example, a solid anticaking agent may be mixed with the salt carrier matrix prior to mixing with the ionene polymer solution. If the additional components are in liquid form they may be added with the ionene polymer solution. The sequence of mixing components in this step is not critical.

As a second step, the moist mass formed in the mixing step is dried to form dry granules. This removes excess liquid from the moist mass prior to tableting. After drying, the granules preferably have a moisture content ranging from about 0.5 to about 5 percent by weight. More preferably, the moisture ranges from about 1 to about 3 percent by weight.

The moist mass may be dried using techniques known in the art. The moist mass may, for example, be dried on trays in hot air ovens, in a fluidized bed dryer, under vacuum, spray dried, or other standard drying techniques. In general, mixtures of a carrier matrix and an ionene polymer are resilient and not necessarily affected by high temperatures.

For heated drying, the temperature may range from about 50° C. to about 80° C. Drying times will vary depending on the moisture content of the moist mass. In general, drying for approximately 3 hours at about 50° C. yields dried granules having a moisture content of about 3 percent by weight. Higher temperatures may be used for shorter drying times. The temperature, however, should not be so high as to decompose or degrade the carrier matrix or the ionene polymer. Preferably, the moist mass may be dried in a hot oven at about 50° C.

Spray drying and fluidized bed drying techniques may be used to accomplish both the mixing and drying steps of the method. An aqueous solution of an ionene polymer may be sprayed onto the salt carrier matrix to form agglomerates. Hot air flows dry the agglomerates driving off volatile components and forming dried granules.

After the drying step is complete, the particle size of the resulting granules are reduced to form a powder. The particle size of the granules may be reduced using grinding or screening techniques known in the art. Depicting a general preferred embodiment, FIG. 1 shows both a grinding and a screening step. Additional grinding or screening steps may be used to reduce the particle size as needed or desired. Grinding may be accomplished using, for example, a Fitz mill or a tornado mill.

Moisture may be absorbed while the size of the dry granules is being reduced. In general, however, any moisture picked up is small or even negligible and does not affect the final tablet.

The particle size of the powder depends upon the size of the tablet to be formed. Larger tablets do not require as small a particle size as smaller tablets. The powder preferably has a particle size of less than 12 mesh and may be about 200 to about 400 mesh or smaller.

The amount of an ionene polymer in the final tablet may be increased by mixing the granules or the powder from the above steps with additional ionene polymer solution to again form a moist mass as described above. This moist mass may then be carried through the method of the invention. In other words, the granules or powder of the ionene polymer/carrier matrix may be recycled through the mixing, drying, and particle size reduction steps to increase the amount of ionene polymer in the final tablet. Mixtures of ionene polymers may also be added in this manner.

Before compressing the powder into a tablet, other tablet components such as those discussed above may be added to the powder in an optional blending step, preferably a dry blending step. Thus, for example, the powder may be blended with various other tablet components such as those discussed above, for example, a disintegration rate regulator, an anticaking agent, a fragrance, a dye and/or other components. Additional grinding and/or screening may also be done after the blending step, if desired or necessary. If liquid formulations are added at this stage, additional drying, grinding and/or screening steps may be used.

The powder, after the size reduction step or the blending step, is then compressed into a tablet. "Compressing" the powder into a tablet may be accomplished by any tablet formation step known in the art. Preferably, as shown in FIG. 1, the powder is compressed into a tablet using pressure. Tableting pressures generally range from about 10 to about 40 tons per square inch.

The amount pressure applied to compress the powder into a tablet should not be too low such that the resulting tablet is weak and without integrity, or for sustained release applications, dissolves too rapidly. If the pressure is too high, the tablet may dissolve too slowly. The actual pressure employed for making a tablet out of any particular powder will depend, to some extent, upon the tablet's end use (quick disintegration or sustained release), its components and their relative proportions in the mixture. In any event, it will be a routine matter to establish the preferred method and/or pressure for tableting ionene polymer/carrier matrix mixtures according to the invention.

It is generally preferred that the pre-compression tablet mixture to be tableted consists only of dry particulate materials, i.e., contains only small amounts of moisture or liquid. In general, up to about 7 percent by weight of moisture or liquid may be tolerated. The pre-compression tablet mixture is the mixture of tablet components prepared during various steps of the method prior to compressing the powder into the tablet. After drying step the moist mass, the pre-compression tablet mixture generally does not take up significant amounts of moisture which would affect the overall tabletization or the final tablet. However, if the amount of moisture hinders the tableting process, additional drying steps may be introduced after any step to reduce the moisture content of the pre-compression tablet mixture. For example, the powder may be dried before compressing it into a tablet. If necessary to reduce particle size, additional grinding and screening steps may also be used.

In the initial tablet formulations, some notable aspects of the tabletizing process were observed. To assist in the practice of the invention, those aspects are discussed below.

As discussed above, excess moisture taken up by the carrier matrix or pre-compression tablet mixture may compromise the compressibility or integrity of the tablets. Thus, one aspect observed was hygroscopicity, or moisture uptake of various pre-compression tablet mixtures. Some initial carrier matrices used included the salt mixtures: sodium chloride/sodium bromide, sodium chloride/lithium bromide and sodium chloride/sodium citrate. These carrier mixtures apparently have a high moisture affinity. However, the carrier mixtures can be effectively utilized by changing the ratio of the salts, more particularly in these cases by increasing the amount of sodium chloride. A good example of suitable carriers matrixes using this combination of salts are those having ratios of 7:2 or 7:3 sodium chloride to sodium bromide, lithium bromide, or sodium citrate. Preferred carrier matrix formulations or pre-compression tablet formulations are those that take the least amount of moisture at ambient relative humidity (60–72%). Accordingly, adjusting the ratio of carrier components can avoid unwanted moisture uptake during the tableting process.

To some extent, all of the pre-compression tablet formulations made were slightly hygroscopic. This generally did not affect the structural integrity of the final tablet. In fact, as discussed below in the Examples, the dried granules may be allowed to stand at ambient relative humidity and absorb moisture to equilibrium before further processing. The resulting tablets took up the least amount of moisture of all formulations. Additionally, some acceptable pre-compression tablet mixtures showed some moisture uptake which decreased over time or stopped entirely. Presumably, these mixtures reached some sort of moisture content equilibrium.

A second aspect observed with some tablets was the apparent loss of the ionene polymer due to migration out of the tablet. This phenomenon apparently occurred in tablets with an improper balance of tablet components. For example, too much disintegration rate regulator with too little carrier matrix made the ionene polymer migrate out of the tablet giving the tablet a sticky feeling. Aside from loss of active ingredient, ionene polymer migration may also cause undesirable interactions with other tablet components. For example, the migrating ionene polymer may interact with a biocidal adjuvant causing both to be deactivated. This migration was corrected by increasing the amount of carrier matrix and/or adding an anticaking agent to the pre-compression tablet formulation.

Tablet appearance, such as color and texture, represents a third aspect observed with initial tablets. Tablet color changes were noted from a white/off white color to shades of brown to reddish pink. In general, the tablets themselves exhibited acceptable hygroscopicity indexes. Tablets having white to off-white color were considered preferable. Some inorganic anti-caking agents such as calcium sulphate, calcium phosphate, and talc may impart more of a gray color to the tablet. Data for tablets showing color changes is shown in Table IV below. Other tablets had a "glossy" appearance due to the stearates, (e.g., magnesium stearate), added as disintegration rate regulators.

A fourth aspect worth noting was the interrelationship between ionene polymer release and tablet disintegration. In general, for example, if 87% of the ionene polymer is released to an aqueous system, then about 87% of the tablet would be expected to have disintegrated. In some tablets if too much disintegration rate regulator was used, the ionene polymer came out as desired, but let only a partially disintegrated tablet behind. This phenomenon was mostly observed in static situations and not turbulent or recirculating situations. Optimally, the tablet should disintegrate uniformly as the product is released. This may be accomplished by adjusting the amount of disintegration rate regulator.

Yet another aspect of the present invention is a method for controlling the growth of microorganisms in an aqueous system capable of supporting such growth. As discussed above, ionene polymers are known to control the growth of microorganisms, biofilm, and slime formation in aqueous systems. The method of the invention uses a tabletized ionene polymer to deliver the ionene polymer to the aqueous system. The tablet may be a quick disintegration or a sustained release tablet depending on the aqueous system and any existing biological fouling. The tablets of the invention are particularly useful in the aqueous systems previously discussed.

According to the present invention, control of the growth of a microorganism in an aqueous system means control to, at, or below a desired level and for a desired period of time for the particular system. This can vary from the complete prevention or inhibition of microorganism growth to control at a certain desired level and/or for a desired time. Controlling the growth of a microorganism includes controlling, and preferably preventing, biofilm and/or slime formation in the aqueous system.

In the method of the invention, the aqueous system is treated with an ionene polymer in an amount effective to control the growth of at least one microorganism in the aqueous system. The ionene polymer is delivered to the aqueous system as a tablet according to the invention. The tabletized ionene polymers of the invention may be used in the same manner as other solid water treatment chemicals. As with other solid water treatment chemicals, the tabletized ionene polymers may be added directly to the aqueous system or placed in device designed to allow controlled contact between the tablet and the aqueous system, for example, a skimmer basket.

The method of the invention can be used in any aqueous system susceptible to the growth of microorganisms. The tabletized ionene polymers of the invention may be employed in aqueous systems used in industrial processes such as metal working fluid systems, papermaking or textile process water systems, cooling water systems (both intake cooling water and effluent cooling water), and waste water systems including waste waters or sanitation waters such as toilet waters or waters undergoing treatment of the waste in the water, e.g. sewage treatment systems. The tabletized ionene polymers may also be used in recreational water systems such as swimming pools or fountains. The following is a more specific discussion directed to some preferred uses and preferred formulations of the tablets of the invention.

Biological fouling in recreational water systems, such as pools, spas, decorative fountains, or water parks, often occurs due to algal growth in the aqueous system. Tablets of the invention designed for this application should deliver an effective amount of ionene polymer to obtain the desired algicidal and/or algistatic effect. The average recommended maintenance dosage is generally 0.5 to 5 ppm per 10,000 gallons of water every 5–7 days (1.6–3.0 mL per cubic meter of water). For spas, a dosage of 0.1 to 0.5 ppm per 1,000 gallons of water is generally recommended. The tablet used may deliver the ionene polymer in a quick release or in a sustained release fashion depending on the needs of the system. Tablet size will vary depending on the type of tablet used (sustained release are generally larger) and whether the tablet contains other biocidal adjuvants such as halogenated compounds. The tablet may or not be colored with water soluble approved FD&C colors such as FD&C blue #1. Fragrances are not usually employed in tablets for use in recreational water systems.

Another common use of solid water treatment chemicals is the treatment of toilet bowl water. Tablets designed for this application should deliver an effective amount of ionene polymer to control, preferably to deter or prevent, bacterial biofilm accumulation and/or the growth of microorganisms. The average dosages of ionene polymer required to in this application generally range between 0.1 to 10 ppm. The tablet may contain additional components could be tabletized in conjunction with the ionene polymer. Desirable components may include, for example, dyes, fragrances, and/or other biocidal adjuvants to broaden the spectrum of biological activity. Sustained release tablets are generally preferred for this application.

Tablets used in cooling water systems preferably deliver between 2–20 ppm of ionene polymer every 1–5 days or as needed to control the growth of microorganisms, for example, to control algal blooms. Sustained release tablets are preferred to maintain water quality while quick release tablets may be used to address exiting biological fouling. The tablet may preferably contain beneficial ingredients such as sodium gluconate and/or sodium bromide commonly used in cooling water applications. Other ingredients such as dyes or fragrances are not generally used in tablets for cooling water systems.

EXAMPLES

The following examples are provided to illustrate, not limit, the present invention.

Example 1

Preparation of a Tabletized Ionene Polymer—Tablet 3

Five grams each of sodium chloride (granular) and anhydrous sodium sulfate were weighed and mixed to form the carrier matrix. Additionally, 0.5 grams of magnesium trisilicate (an anticaking agent) was added to this salt mixture and mixed with a mortar and pestle to obtain a uniform powder. Subsequently, 2 grams of BUSAN® 1157 product was added and mixed to obtain a homogeneous moist mass.

The ionene polymer in BUSAN® 1157 product is a reaction product of dimethylamine with epichlorohydrin, cross-linked with ethylenediamine. Referring to formula II, the ionene polymer has substituents where $R^1$ and $R^2$ are each methyl, A is —$CH_2CH(OH)CH_2$— and $X^-$ is $Cl^-$. The ionene polymer has a 100,000–500,000 average molecular weight. BUSAN® 1157 product is available from Buckman Laboratories, Inc. in a 50% aqueous dispersion.

After the mixing step, the mixture was dried in a 50° C. oven for approximately 3 hours. The dried granules were then ground with a mortar and pestle to obtain a fine powder. The ionene polymer/carrier mixture was then compressed into tablets (32 mm in diameter and 8.5 mm in width) with manual carver press (Model C). The resulting tablet, Tablet 3 in Table I below, weighed 10.8 grams.

The tablet was placed in an open dish and monitored at ambient room conditions, (23°–25° C. and 70 percent humidity) for 28 days to determine the degree of hygroscopicity. The tablet weight increased only 0.15 grams, a hygroscopicity index of 1.4%. The tablet was, therefore, considered to be a preferred tablet of the invention.

Example 2

Preparation of a Tabletized Ionene Polymer—Tablet 4

Five grams each of sodium chloride (granular) and anhydrous sodium sulfate were weighed and mixed to form the carrier matrix. Additionally, 0.5 grams of magnesium trisilicate (an anticaking agent) was added to this salt mixture and mixed using a mortar and pestle to obtain a uniform powder. Subsequently, 2 grams of BUSAN® 1157 product was added and mixed to obtain a homogeneous moist mass. The moist mass was then dried in a 50° C. oven for approximately 3 hours. The dried granules were then ground using a mortar and pestle to obtain a fine powder. The powder was then blended with 0.5 grams of stearic acid (a disintegration rate regulator). The resulting mixture was then compressed into tablets (32 mm in diameter and 8.5 mm in width) with manual carver press (Model C). The resulting tablet, Tablet 4 in Table I, weighted 10.7 grams.

Monitoring its weight at ambient room conditions as in Example 1 for 48 days to determine degree of hygroscopicity, the tablet weight increased only 0.041 grams. Tablet 4 having a hygroscopicity index of 0.12 was, therefore, considered to be a most preferred tablet of the invention.

Example 3

Preparation of a Tabletized Ionene Polymer—Tablet 14

Five grams each of sodium chloride (granular) and anhydrous sodium sulfate were weighed and mixed to form the carrier matrix. Additionally, 0.5 grams of magnesium trisilicate (an anticaking agent) was added to this salt mixture and mixed with a mortar and pestle to obtain a uniform powder. Subsequently, 2 grams of BUSAN® 1157 product was added and mixed to obtain a homogeneous moist mass. At this stage, the moist mass was dried in a 50° C. oven for approximately 3 hours. The resulting dry granules were then ground using mortar and pestle to obtain a fine powder. The powder was then blended using a mortar and pestel with 0.5 grams of stearic acid (a disintegration rate regulator), 1.0 gram of polyoxyethylene-2-stearyl ether (a disintegration rate regulator) and 1.0 gram of trichloro-s-triazinetrione (a biocidal adjuvant, ACL 90 plus product available from Occidental Chemical Corporation). The resulting mixture was then compressed into tablets (32 mm in diameter and 8.5 mm in width) with manual carver press (Model C). The resulting tablet, Tablet 14 in Table II, weighed 13.0 grams. Monitoring its weight at ambient room conditions as in Example 1 to determine its degree of hygroscopicity. Tablet 14 increased in weight 0.129 grams over 30 days. Tablet 14, with a hygroscopicity index of 0.60, was considered to be a preferred tablet of the invention.

Tables I, II, III, and IV present additional data relating to other tablets of the invention. The tablets were prepared and evaluated using the same procedures as described in Examples 1 through 3 above. Except as noted, 2 grams of the ionene polymer solution used in these tablets was BUSAN® 1157 product available from Buckman Laboratories Inc., Memphis, Tenn.

The following abbreviations are used in Tables I–IV: ACA=anticaking agent, DRR=disintegration rate regulator, ITW=initial tablet weight, and HI=hygroscopicity index. Other abbreviations refer to specific components. Polyoxy refers to polyoxyethylene-2-stearyl ether, a disintegration rate regulator. ARMID 18 is ARMID 18 product, a fatty acid used as a disintegration rate regulator and available from Akzo Chemical Co., Cooke, Ill. Oxazolidinone refers to 5-chloromethyl-2-oxazolidinone, a disintegration rate regulator. Mono-quat refers to BTC 2125MP40 product, a biocide containing 40 percent of a mixture of alkyldimethylbenzylammonium chloride and alkyldimethylethylbenzylammonium chloride available from Stepan Chemicals, Northfield, Ill. Chlorhexidine diacetate is the biocidal adjuvant 1,1-hexamethylenebis[5-(4-chloro-2-phenyl)biguanide]diacetate available from Lonza Chemical Co., Fairlawn, N.J. Other biocidal adjuvants used in the tablets include trichloro-s-triazonetrione, calcium hypochlorite, and sodium borate. The tables list the color of the tablets as follows: W=White, OW=Off white, DW=Dull white, LB=Light Brown, B=Brown, and PK=pink. Other notes follow each table.

TABLE I

| Carrier Matrix | TABLET COMPOSITIONS (wt in grams) | | | | | | | | | | |
|---|---|---|---|---|---|---|---|---|---|---|---|
| | 1 | 2 | 3 | 4 | 5 | 6 | 7 | 8 | 9 | 10 | 11 |
| Sodium chloride | 5 | 5 | 5 | 5 | 5 | 5 | 5 | 5 | 5 | 5 | 5 |
| Sodium sulphate | 5 | 5 | 5 | 5 | 5 | 5 | 5 | 5 | 5 | 5 | 5 |
| ACA | | | | | | | | | | | |
| Magnesium trisilicate | 1.0 | 0.5 | 0.5 | 0.5 | 0.5 | 0.5 | 0.5 | 1.0 | 0.5 | 0.5 | |
| Oxazolidinone | | | | | | 0.5 | | | | | |
| Microcrystalline cellulose | | | | | | | | | | | 0.5 |
| DRR | | | | | | | | | | | |
| Stearic acid | | | | 0.5 | 0.5 | | 1.0 | | | | 1.0 |
| Magnesium stearate | 0.5 | 0.5 | | | | 0.5 | | | 0.5 | | |
| Hexaglyceryl distearate | | | | | | | | 0.5* | | | |
| Polyoxy | | 0.5 | | | | | | | | 1.0 | 1.0 |
| Potassium stearate | | | | | 0.5 | | | | | 0.5 | |
| Other additives | | | | | | | | | | | |
| Sodium Perborate | | | | | | | | | | | 1.0 |
| ITW | 12.3 | 12.1 | 9.9 | 10.8 | 10.9 | 10.8 | 11.8 | 11.3 | 12.5 | 12.7 | 12.5 |
| HI (% by wt)/(days) | .34/49 | .28/49 | 1.4/28 | .12/48 | .68/46 | .72/52 | .75/48 | .20/52 | .84/46 | .20/48 | .07/30 |
| Rating: | MP | MP | P | MP | MP | MP | MP | MP | MP | MP | MP |
| Tablet Color | W | W | OW | DW | W | W | OW | W | W | W | W |

Table I notes:
* = added to carrier matrix prior to mixing step

TABLE II

| Carrier Matrix | TABLET COMPOSITIONS (wt in grams) | | | | | | | | |
|---|---|---|---|---|---|---|---|---|---|
| | 12 | 13* | 14 | 15 | 16 | 17 | 18 | 19 | 20 |
| Sodium chloride | | 5 | 5 | 5 | 5 | 5 | 5 | 5 | 5 |
| Sodium sulphate | 2.5 | 5 | 5 | 5 | 5 | 5 | | 5 | 5 |
| CaSO₄ | 2.5 | | | | | | | | |
| Sodium Gluconate | | | | | | | 5 | | |
| ACA | | | | | | | | | |
| Magnesium trisilicate | 1.0 | 0.5 | 0.5 | 0.5 | | | 0.5 | 0.5 | 0.5 |
| Magnesium oxide | | | | | 0.2 | | | | |
| Zinc oxide | | | | | | | 0.5 | | |
| DRR | | | | | | | | | |
| Stearic acid | 0.5 | 0.5 | 1.0 | | 1.0 | 1.0 | 0.5 | 0.3 | 0.3 |
| Polyoxy | 0.5 | 1.0 | 1.0 | 1.0 | 1.0 | 1.0 | | | |
| ARMID 18 | | | | 1.0 | | | | | |
| Other additives | | | | | | | | | |
| Trichloro-s-tiazinetrione | | | 1.0 | | | | | | |
| Calcium hypochlorite | | | | | | 1.0 | | | |
| Mono-quat | | | | | | | | 1.0 | |
| Chlorhexidine diacetate | | | | | | | | | 1.0 |

TABLE II-continued

| | TABLET COMPOSITIONS (wt in grams) | | | | | | | | |
|---|---|---|---|---|---|---|---|---|---|
| Carrier Matrix | 12 | 13[a] | 14 | 15 | 16 | 17 | 18 | 19 | 20 |
| ITW | 7.3 | 12.1 | 13.0 | 11.5 | 11.9 | 13.4 | 10.9 | 11.5 | 11.7 |
| HI (% by wt)/(days) | 1.5/44 | 0[b]/44 | .60/30 | 0[b]/45 | 1.5/28 | 0[b]/30 | 1.0/32 | 2.1/17 | 1.8/17 |
| Rating: | P | MP | MP | MP | P | MP | P | (P)[c] | (P)[c] |
| Tablet color: | W | OW | W | OW | OW | W | W | W | W |

Table II notes:
[a] = dried granules allowed to stand at room ambient conditions overnight,
[b] = tablet showed slight weight loss,
[c] = 17 day measurement

TABLE III

| TABLET COMPOSITIONS (wt in grams) | | | | |
|---|---|---|---|---|
| Carrier matrix | 21 | 22 | 23[a] | 24[b] |
| Sodium chloride | 5.0 | | 5.0 | 5.0 |
| Sodium sulphate | 5.0 | | 5.0 | 5.0 |
| Calcium sulphate | | 5.0 | | |
| ACA | | | | |
| Magnesium trisilicate | 0.2 | 1.0 | 0.5 | 0.5 |
| DRR | | | | |
| Stearic acid | 0.2 | 0.5 | 1.0 | 0.5 |
| Polyoxy | | 1.0 | | |
| Other additives | | | | |
| Sodium Perborate | | | | 0.5 |
| ITW | 10.4 | 7.2 | 11.7 | 11.6 |
| HI (% by wt)/(days) | 1.5/24 | 1.8/44 | 1.2/32 | 2.0/32 |
| Rating: | P | P | P | P |
| Tablet color: | OW | W | OW | OW |

Table III notes:
a = To increase the ionene polymer content, an additional 1 gram of BUSAN ® 1157 product was added to the powder after the initial mixing, drying and grinding steps. Tablet 23 was then prepared according to the method of the invention shown in Examples 1–3.
b = To increase the ionene polymer content, an additional 2 grams of BUSAN ® 1157 product was added to the powder after the initial mixing, drying and grinding steps. Tablet 24 was then prepared according to the method of the invention shown in Examples 1–3.

TABLE IV

COLORED TABLETS

| | TABLET COMPOSITIONS (wt in grams) | | | | |
|---|---|---|---|---|---|
| Carrier Matrix | 25 | 26 | 27 | 28 | 29 |
| Sodium chloride | 5 | 5 | 10 | 2.5 | 5 |
| Sodium sulphate | 5 | 5 | | 5 | 5 |
| Sorbic acid | | | 0.5 | 2.5 | |
| Benzoic acid | 0.5 | | | | |
| ACA | | | | | |
| Aluminum hydroxide | | 0.2[a] | | | |
| Magnesium trisilicate | 0.5[a] | | | | |
| DRR | | | | | |
| Stearic acid | | 1.0 | 1.0 | 1.0 | 1.0 |
| Polyoxy | 0.5 | | | 1.0 | |
| Other additives | | | | | |
| Titanium dioxide | | | | | 0.5[a] |
| ITW | 10.3 | 10.1 | 11.1 | 11.6 | 11.0 |
| HI (% by wt)/(days) | .91/42 | .78/35 | .86/22 | 1.4/29 | .81/35 |

TABLE IV-continued

COLORED TABLETS

| | TABLET COMPOSITIONS (wt in grams) | | | | |
|---|---|---|---|---|---|
| Rating: | MP | MP | MP | P | MP |
| Tablet Color | OB | PK | OB | OB | PK |

Table IV notes:
[a] = component added into powder in a dry blending step prior to tablet compression

Example 4

Determination of Moisture Content

The moisture content of the ionene polymer/carrier mixture after various steps in the tabletization process was measured using the following standard procedure. An empty, dry plastic beaker was weighed. A sample whose moisture content was being measured was placed in the beaker and the beaker plus sample weighed. The beaker plus sample was placed in an oven heated to at least 105° C. for at least one hour or until the sample was completely dry—a constant dry weight obtained. The beaker plus sample was then weighed. The amount of moisture in the original sample was determined from the difference in weight prior to drying and after drying. The amount of moisture was expressed as a weight percentage of the original sample before drying. The moisture content for two mixtures of ionene polymer/carrier according to the invention is shown in Table V.

TABLE V

| Percent Moisture content (specifications) | | |
|---|---|---|
| Measurements | Tablet 1 | Tablet 3 |
| 1 Mixing step: moist cake | 8.3 | 7.9 |
| 2 Drying step: dried granules | 1.7 | 1.4 |
| 3 Direct compression: final blend & tabletized | 2.3 | 1.8 |

Example 5

Ionene polymer Release Rate Determination

Tablet 10 was chosen to determine the release rate of ionene polymer from a tablet of the invention while in an aqueous system. The tablet was placed in a beaker containing 2 liters of water. A solution containing an equivalent amount of ionene polymer per milliliter was prepared as the standard solution containing BUSAN® 1157 product. The quantity of ionene polymer released was determined by titrating an aliquot from each solution with Poly (vinylsulfate, potassium salt), (PVSAK). This method is the basis for the widely used Taylor Polyquat/QAC Test Kit. Toluidine Blue O indicator changes from blue to purple at the end point. A useful literature reference for this analytical method is: L. K. Wang and W. W. Schuster, *Ind. Eng. Prod. Res. Dev.* Vol. 14, No. 4, pp 312–314, (1975). The aliquot size was selected to give a titration of about one half of a buret full (5.0 mL) with the PVSAK used for the standard solution.

Figure 2:
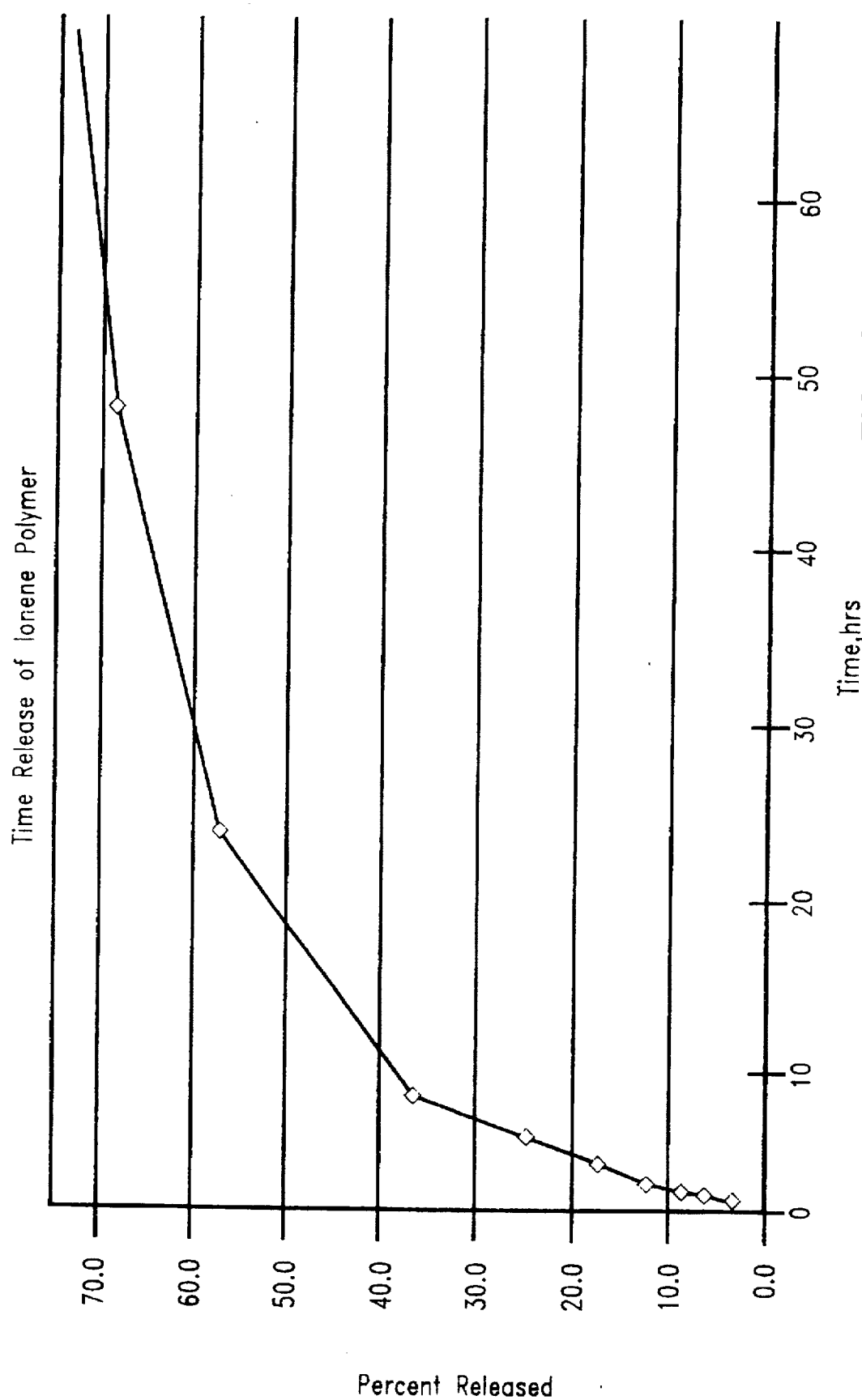
FIG. 2 depicts the release rate of an ionene polymer from a tablet of the invention as discussed in Example 4.

Air was bubbled into the sample solution during the test to continuously mix the solution. An aliquot was removed at various time intervals for later analysis for ionene polymer concentration. Table VI below summarizes the data obtained. FIG. 2 show a plot of this data.

TABLE VI

| Percent Ionene Polymer Released | |
|---|---|
| Time (hrs) | Tablet 10 |
| 0.17 | 1.7 |
| 0.5 | 9.0 |
| 1 | 11.0 |
| 2 | 16.4 |
| 4 | 25.0 |
| 8 | 36.1 |
| 24 | 58.5 |
| 48 | 69.5 |
| 72 | 71.2 |

The claimed invention is:

1. A method of making a tabletized ionene polymer composition comprising the steps of:

mixing an aqueous solution or dispersion of an ionene polymer with a salt carrier matrix to form a moist mass, drying the moist mass to form dry granules, reducing the size of the granules to form a powder, and compressing the powder into a tablet, wherein the resulting tablet absorbs no more than 3 percent by weight moisture upon standing for 30 days in air at approximately 25° C. and approximately 70 percent humidity, wherein the weight ratio of solution or dispersion to carrier matrix in the mixing step is from about 1:10 to 4:10.

2. A method of claim 1, further comprising, after the reducing step and prior to the compressing step, the step of blending a disintegration rate regulator to the powder.

3. A method of claim 1, further comprising, before the mixing step, the step of combining an anticaking agent with the carrier matrix.

4. A method of claim 1, further comprising, after the reducing step and prior to the compressing step, the step of blending a disintegration rate regulator, an anticaking agent, a biocidal adjuvant, a dye, or a perfume into the powder.

5. A method of claim 1, wherein the reducing step comprises a grinding step and screening step prior to the compressing step.

6. A method of claim 1, prior to the reducing step, further comprising the steps of:

mixing the granules with an aqueous solution of an ionene polymer to form a second moist mass, and drying the second moist mass to form dry granules.

7. A method of claim 1, prior to the compressing step, further comprising the steps of:

mixing the granules with an aqueous solution of an ionene polymer to form a second moist mass, and drying the second moist mass to form dry granules.

8. A method of claim 1, wherein the carrier matrix comprises sodium acetate, sodium bicarbonate, sodium borate, sodium bromide, sodium carbonate, sodium chloride, sodium citrate, sodium fluoride, sodium gluconate, sodium sulfate, calcium chloride, calcium lactate, calcium sulfate, potassium sulfate, tripotassium phosphate, potassium chloride, potassium bromide, potassium fluoride, magnesium chloride, magnesium sulfate, lithium chloride or mixtures thereof.

9. A method of claim 8, wherein the ionene polymer comprises a repeating unit of the formula I:

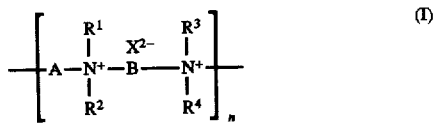

wherein $R^1$, $R^2$, $R^3$, and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group;

A is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, symmetric or asymmetric di-$C_1$–$C_{10}$-alkyleneether, arylene, arylene-$C_1$–$C_{10}$-alkylene, or $C_1$–$C_{10}$-alkylenearyl-$C_1$–$C_{10}$-alkylene;

B is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, arylene, arylene-$C_1$–$C_{10}$-alkylene, or $C_1$–$C_{10}$-alkylenearyl-$C_1$–$C_{10}$-alkylene; and $X^{2-}$ is a divalent counter ion, two monovalent counter ions or a fraction of a polyvalent counter ion sufficient to balance the cationic charge in the repeating unit of said ionene polymer.

10. A method of claim 8, wherein the ionene polymer comprises a repeating unit of formula II:

wherein $R^1$ and $R^2$ can be identical or different, and are selected from H, $C_1$–$C_{20}$ alkyl optionally substituted with at least one hydroxyl group, and benzyl optionally substituted on the benzene moiety with at least one $C_2$–$C_{20}$ alkylene group;

A is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, symmetric or asymmetric di-$C_1$–$C_{10}$-alkyleneether, arylene, arylene-$C_1$–$C_{10}$-alkylene, or $C_1$–$C_{10}$-alkylenearyl-$C_1$–$C_{10}$-alkylene; and $X^-$ is a monovalent counter ion, one-half of a divalent counter ion or a fraction of a polyvalent counter ion sufficient to balance the cationic charge of the repeating unit in said ionene polymer.

11. A method of claim 8, wherein the ionene polymer comprises a repeating unit of formula III:

$$+R-B'+_n \qquad (III)$$

wherein R is

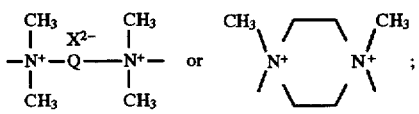

Q is $-(CHR')_p-$, $-CH_2-CH=CH-CH_2-$, $-CH_2-CH_2-O-CH_2-CH_2-$, $-CH_2-CH(OH)-CH_2-$, or $-(CHR')_n-NH-C(O)-NH-(CHR')_n-$; and B' is $\{-[CH_2-CH(OH)-CH_2-N^+R'_2-(CHR')_n-NH-C(O)-NH]-, X^-\}$ or $\{-[(CHR')_n-N^+R'_2-CH_2-CH(OH)-CH_2]-, X^-\}$; n and p vary independently from 2 to 12; each R' is independently hydrogen or a lower alkyl group; $X^{2-}$ is a divalent counter ion, two monovalent counter ions or a fraction of a polyvalent counter ion sufficient to balance the cationic charge in said group R; and $X^-$ is a monovalent counter ion, one-half of a divalent counter ion or a fraction of a polyvalent counter ion sufficient to balance the cationic charge in said group B'.

12. A method of claim 11, wherein R' is hydrogen or $C_1$-$C_4$, n is 2–6, and p is 2–6; wherein R' is hydrogen or methyl, n is 3, and p is 2; or wherein R is urea diamine, B' is $-CH_2CH(OH)CH_2-$, and $X^-$ is $Cl^-$.

13. A method of claim 1, wherein the granules are reduced to a powder having a particle size of 12 mesh or smaller.

* * * * *

UNITED STATES PATENT AND TRADEMARK OFFICE
CERTIFICATE OF CORRECTION

PATENT NO. : 5,709,880
DATED : January 20, 1998
INVENTOR(S) : L. Fernando DEL CORRAL et al.

It is certified that error appears in the above-indentified patent and that said Letters Patent is hereby corrected as shown below:

Add claim
-- 14. A method of claim 1, wherein the weight ratio of solution or dispersion to carrier matrix in the mixing step is from about 1:10 to about 2:10. --

Signed and Sealed this

Sixteenth Day of June, 1998

Attest:

BRUCE LEHMAN

*Attesting Officer*  *Commissioner of Patents and Trademarks*